United States Patent
Hattingh et al.

(10) Patent No.: US 9,804,183 B2
(45) Date of Patent: Oct. 31, 2017

(54) APPARATUS AND METHOD FOR LIQUID SAMPLE INTRODUCTION

(71) Applicant: Thermo Electron Manufacturing Limited, Cambridge (GB)

(72) Inventors: Ruan Hattingh, Cambridge (GB); Neil Bird, Cambridge (GB); Paul Neal, Cambridge (GB); Olivier Moteau, Cambridge (GB); Andrew Clark, Cambridge (GB)

(73) Assignee: Thermo Electron Manufacturing Limited, Cambridge (GB)

( * ) Notice: Subject to any disclaimer, the term of this patent is extended or adjusted under 35 U.S.C. 154(b) by 504 days.

(21) Appl. No.: 14/163,541

(22) Filed: Jan. 24, 2014

(65) Prior Publication Data

US 2014/0283627 A1   Sep. 25, 2014

(30) Foreign Application Priority Data

Mar. 25, 2013 (GB) .................................. 1305405.1

(51) Int. Cl.

| | |
|---|---|
| *G01N 1/00* | (2006.01) |
| *G01N 35/10* | (2006.01) |
| *B01L 3/02* | (2006.01) |
| *B05B 17/06* | (2006.01) |
| *H01J 49/04* | (2006.01) |
| *G01N 21/31* | (2006.01) |
| *G01N 21/64* | (2006.01) |
| *G01N 1/38* | (2006.01) |

(52) U.S. Cl.
CPC ............ *G01N 35/10* (2013.01); *B01L 3/0268* (2013.01); *B05B 17/0615* (2013.01); *G01N 21/3103* (2013.01); *G01N 21/6404* (2013.01); *H01J 49/0454* (2013.01); *B01L 2300/0829* (2013.01); *B01L 2400/0433* (2013.01); *G01N 1/38* (2013.01); *G01N 2035/1034* (2013.01)

(58) Field of Classification Search
CPC ............... G01N 35/10; G01N 21/3103; G01N 21/2604; G01N 1/38; G01N 2035/1034; B01L 3/0268; B01L 2300/0829; B01L 2400/0433
USPC ...................................................... 73/864.81
See application file for complete search history.

(56) References Cited

U.S. PATENT DOCUMENTS

| | | | |
|---|---|---|---|
| 3,521,795 A | 7/1970 | Fassel et al. | |
| 3,775,058 A | 11/1973 | Bush | |

(Continued)

FOREIGN PATENT DOCUMENTS

| | | |
|---|---|---|
| CN | 2716833 V | 8/2005 |
| CN | 101247870 A | 8/2008 |

(Continued)

*Primary Examiner* — John Fitzgerald
*Assistant Examiner* — Rodney T Frank
(74) *Attorney, Agent, or Firm* — A. J. Gokcek

(57) ABSTRACT

A method and apparatus for introducing droplets of liquid sample into an analysis device using a gas stream, the droplets being produced by the application of acoustic energy to a quantity of liquid sample. Acoustic energy may be applied to a quantity of liquid sample located on a solid surface of a sample support so as to eject a droplet of sample from the quantity of sample; the droplet of sample may be entrained in a gas stream; and the droplet of sample may be transported into the analysis device using the gas stream.

16 Claims, 5 Drawing Sheets

(56) References Cited

U.S. PATENT DOCUMENTS

Figure 1:
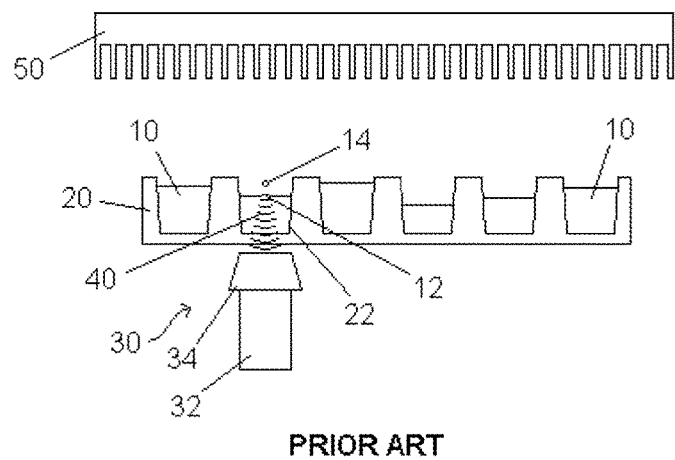

| | | | |
|---|---|---|---|
| 4,801,411 A | 1/1989 | Wellinghoff et al. | |
| 5,345,079 A | 9/1994 | French et al. | |
| 7,275,807 B2 | 10/2007 | Van Tuyl | |
| 7,834,225 B1 | 11/2010 | Adiga et al. | |
| 2002/0109084 A1* | 8/2002 | Ellson | H01J 49/0454 250/288 |
| 2004/0026615 A1 | 2/2004 | Ellson et al. | |
| 2004/0102742 A1 | 5/2004 | Van Tuyl | |
| 2005/0221339 A1 | 10/2005 | Griffiths et al. | |
| 2006/0071983 A1 | 4/2006 | Stearns et al. | |
| 2006/0110833 A1 | 5/2006 | Agnes et al. | |
| 2006/0280866 A1 | 12/2006 | Marquez et al. | |
| 2012/0145890 A1 | 6/2012 | Goodlett et al. | |
| 2013/0175356 A1 | 7/2013 | Gellert | |

FOREIGN PATENT DOCUMENTS

| | | |
|---|---|---|
| CN | 101675220 A | 3/2010 |
| DE | 102 60 071 A1 | 7/2004 |
| EP | 2516999 B1 | 10/2012 |
| WO | 0247820 A2 | 6/2002 |
| WO | 2011076774 A1 | 6/2011 |

* cited by examiner

APPARATUS AND METHOD FOR LIQUID SAMPLE INTRODUCTION

FIELD OF THE INVENTION

This invention relates to the field of liquid sample introduction systems for analytical instruments and relates to those analysis devices for which sample must be introduced in the form of a stream of droplets. The invention relates to a means for utilizing an acoustic droplet generator for producing droplets for direct injection into an analysis device.

BACKGROUND

Liquid sample supplied to an analysis device in the form of droplets is usually provided using a nebulizer to generate an aerosol. Analysis devices which utilize such droplets include ionization and/or excitation sources such as microwave induced plasma (MIP), inductively coupled plasma (ICP) and flames. The analysis devices provide spectrometers which perform MIP and ICP optical emission spectrometry (OES), MIP and ICP mass spectrometry (MS), atomic absorption spectrometry (AA) and atomic fluorescence spectroscopy (AFS). Typically the sample-containing liquid is formed into a stream of droplets using a nebulizer utilizing a stream of inert gas such as argon. Nebulizers produce droplets with a wide range of sizes. However where the analysis device utilizes a plasma or flame to dissociate and excite or ionize the sample, as both plasmas and flames are inefficient at dissociating large droplets, a spray chamber is usually placed between the nebulizer and the torch so as to exclude large droplets from the sample stream entering the analysis device. The spray chamber filters the stream of droplets by causing the flow to follow a tortuous path such that the larger droplets impinge upon surfaces in the spray chamber and are drained away, smaller droplets being carried by the flow of gas into the torch. In the cases of ICP-OES and ICP-MS it is well known that only 1-2% of the nebulized sample-containing liquid is in the form of sufficiently small droplets suitable for processing within the torch, and that this form of sample introduction is therefore inefficient.

Alternative methods of producing a stream of sample droplets include the use of continuous fluid jet micro-droplet generator (G. M. Hieftje and H. V. Malmastadt, Analytical Chemistry, Vol. 40, pp. 1860-1867, 1968) and vibrating orifice monodisperse aerosol generator (H. Kawaguchi et al., Spectrochimica Acta, vol. 41 B, pp. 1277-1286, 1986, T. Nomizu et al., Journal of Analytical Atomic Spectrometry, vol. 17, pp. 592-595, 2002), The ability to produce droplets one at a time and thereby more completely control the droplet ejection process—so-called "droplet-on-demand" techniques—have long been seen as desirable. Where the droplet generator is of a type in which the droplet generation apparatus enables a single droplet to be ejected in response to a control signal, the droplet generator is one of a class of generators termed droplet-on-demand generators. An early generator with this capability designed principally for inkjet printing was a piezoelectrical droplet generator (U.S. Pat. No. 3,683,212). Such a droplet generator was employed to create a stream of droplets containing sample material, the droplets being passed through an oven so as to make the droplet evaporate to complete or partial dryness before injection into an ICP in order to study oxide ion formation (J. B. French, B. Etkin, R. Jong, Analytical Chemistry, Vol. 66, pp. 685-691, 1994). This coupling of the piezoelectric droplet generator and oven was termed the monodisperse dried microparticulate injector (MDMI) and such systems have been used in other studies (J. W. Olesik and S. E. Hobbs, Analytical Chemistry, vol. 66, pp. 3371-3378, 1994; A. C. Lazar and P. B. Farnsworth, Applied Spectroscopy, vol. 53, pp. 457-470, 1999; A. C. Lazar and P. B. Farnsworth, Applied Spectroscopy, vol. 51, pp. 617-624, 1997). Use of the piezoelectric droplet generator without the desolvation in an oven has been successfully implemented as a sub-nanoliter sample introduction technique for Laser-Induced Breakdown Spectroscopy and Inductively Coupled Plasma Spectrometry (S. Groh et al., Analytical Chemistry, vol. 82, pp. 2568-2573, 2010; A. Murtazin et al., Spectrochimica Acta, vol. 67B, pp. 3-16, 2012).

All these droplet generation devices require liquid sample to be fed into an enclosed volume within the droplet generation device. Typically sample is prepared and stored in vessels, and the vessels are usually stored in an array close to the analysis device, so that the vessels may be accessed by an autosampler. The autosampler positions a take-up tube within one of the vessels, and sample is drawn into the tube and transported into the droplet generator using suction. Hence the sample-containing liquid comes in contact with the take-up tubing and with the internal surfaces of the droplet generator. Once the sample take-up is complete, the autosampler withdraws the take-up tubing from the sample-containing vessel and moves it to a vessel containing wash solution. Wash solution is drawn into the take-up tubing and into the droplet generator and flushed to waste in order to wash out the remains of the previous sample before the next sample is admitted. For all the droplet generation devices described above, whether or not an autosampler is utilized, means such as tubing to transfer sample-containing liquid from a storage vessel is required and the droplet generator itself presents exposed surfaces to the sample-containing liquid.

Due to the increasingly routine use of spectrometry, sample throughput has become one of the most important requirements as often it is this which ultimately determines the cost-per-analysis in routine applications. With the increased sensitivity of instrumentation and automated sample handling, sample throughput is largely limited not by the sample introduction or analysis time but rather by memory effects caused by deposition of material from the previous sample on components of the sample introduction system and spectrometer. Due to the increased sensitivity of the spectrometers and their ultimate detection limits, material deposited upon the sample introduction system is gradually washed away during the "wash" cycle described above, and typically at least 40-60 seconds is needed after each sample to reduce memory effects below an acceptable threshold. In addition, the time to transport liquid from a containment vessel to the droplet generator may be significant, adding time both for sample uptake and wash solution uptake.

Development of instrumentation has increased the sensitivity of analysis devices and frequently sample solutions require dilution. Various methods for automatic dilution of samples have been devised (as described for example in U.S. Pat. No. 7,998,434). In order to monitor and correct for variations in accuracy, internal standards are often used. Both dilution and addition of standards requires the mixing of liquids prior to introduction to the analysis device. With all the droplet generation devices above, typically the liquids to be mixed are either mixed within a vessel prior to take-up, or are mixed at a location between the vessels containing the liquids and the droplet generator. As such, additional liquid handling devices or process steps are required, and additional vessels or separate mixing devices are required. Any mixing devices and associated liquid containment conduits must also be washed out prior to their next use.

Acoustic droplet ejection systems have been developed utilising a phenomenon first reported by R. W. Wood and A. Loomis in 1927 [Philiosophical Magazine, 4 (22), 417-436]. Acoustic energy emitted from a transducer can be converted to kinetic energy in a liquid. If acoustic energy is focused near a free surface of the liquid, droplets may be ejected from the surface of the liquid, the droplet size scaling inversely with the frequency of the acoustic energy. Droplet volumes from ~20 pl to 2 µl and droplet ejection rates of hundreds of droplets per second may be produced. Unlike other droplet ejection devices, no contact between the sample liquid and the droplet ejector or sampling apparatus such as nozzles, pipette tips or pin tools occurs. Prior art acoustic droplet ejectors have been used to eject droplets upwards from well plates to be deposited onto solid surfaces or receiving plates located immediately above the well plates. Hence droplets are transferred from containment vessels onto receiving vessels in relatively close proximity.

SUMMARY OF THE INVENTION

In light of the above, the present invention has been made.

In a first independent aspect, the present invention provides a method of introducing liquid sample into an analysis device comprising the steps of: applying acoustic energy to a quantity of liquid sample located on a solid surface of a sample support so as to eject a droplet of sample from the quantity of sample; entraining the droplet of sample in a gas stream; and transporting the droplet of sample into the analysis device using the gas stream.

In a further independent aspect, the present invention provides a sample introduction system for an analysis device comprising: a solid surface of a sample support suitable for locating a quantity of liquid sample; an acoustic transducer arranged so that, in use, acoustic energy is emitted towards the solid surface; a gas supply arranged to supply a stream of gas; and a gas conduit arranged between the gas supply and the sample support and between the sample support and an inlet of the analysis device.

In use, a quantity of liquid sample is located on a solid surface and acoustic energy from an acoustic transducer is directed towards the liquid sample. The acoustic energy causes a droplet of liquid sample to be ejected from a free surface of the quantity of liquid sample. A gas stream is directed so as to entrain the droplet of sample and transport the droplet away from the quantity of liquid sample on the solid surface and into an analysis device. Means for directing the gas stream so as to entrain the droplet of sample and preferably transport it so that it does not come into contact with any surfaces along a transport path between the quantity of liquid sample and the analysis device are herein described.

Preferably the droplet of sample is transported into the analysis device along a transport path and the droplet of sample does not contact any solid surface along the transport path after leaving the quantity of sample and before entering the analysis device. Preferably gas stream enters the analysis device as it enters a sample inlet. Preferably the droplet of sample entrained in the gas stream enters the analysis device and sample material within the entrained droplet of sample is excited or ionized within the analysis device without having come into contact with any solid surface on its journey from the quantity of sample.

In some embodiments the quantity of sample is located on the solid surface of a sample support within a containment vessel, preferably the containment vessel is one of an array of containment vessels, the sample support comprising the array of containment vessels; more preferably the quantity of sample is located on the solid surface of a sample support within a well plate. Preferably the sample support comprises a plurality of sample support sites, such as containment vessels, indentations, protuberances, or sites having undergone surface treatment such as etching or impregnation. In some embodiments the quantity of sample is located on the solid surface of a sample support in the form of a liquid drop, in which case the sample support may not comprise a containment vessel, but may be, for example, a flat glass slide or a local surface protuberance or other localized site.

The solid surface preferably comprises an inert material; preferably the inert material comprises one or more of: polystyrene, PFA, LCP, PTFE, Nylon, PEEK, ceramic or glass.

Preferably the acoustic energy is applied to the quantity of sample through the solid surface of the sample support. Preferably the acoustic transducer is arranged so that, in use, acoustic energy is emitted towards a first surface of the sample support and the quantity of liquid sample is located upon a second surface of the sample support, the second surface being different from the first surface. In some embodiments the acoustic transducer is arranged to emit acoustic energy through a side wall of a containment vessel, and the quantity of sample is located within the containment vessel. Preferably the first and second surfaces of the sample support are substantially parallel to one another. Preferably, in embodiments in which the sample support comprises a containment vessel, the first surface is arranged, in use, to be a downward side of the sample support and the second surface is arranged to be an upward side of the sample support; most preferably the second surface is inside the containment vessel and is the inside lower surface of the containment vessel. Where the sample support comprises a flat plate, and the quantity of sample is located upon one side of the flat plate (the second surface), the first surface is arranged, in use, to be the other side of the sample support.

A gas supply is arranged to supply a stream of gas. The gas stream preferably comprises inert gas. More preferably the gas substantially only comprises inert gas. Preferably the gas comprises one or more of: $N_2$, He, Ar, $SF_6$, Xe, Ne, Kr. The gas flow rate is preferably between 0.1 and 3 $l \cdot min^{-1}$ at a pressure between 0.1 and 2 bar. The gas may be at any suitable temperature, lower temperatures being beneficial where the liquid sample comprises volatile substances. Preferably a flow of inert gas is directed at the quantity of sample on the solid surface immediately prior to applying the acoustic energy to the quantity of sample.

In other embodiments, such as those in which the analysis device is an atomic absorption spectrometer, the gas is preferably a pre-mixed mixture of the desired oxidant and fuel gases in the appropriate ratios, or is one of the desired oxidant and the desired fuel gas.

In some preferred embodiments a gas stream is supplied at a first flow rate whilst transporting the droplet of sample, and a gas stream is supplied at a second flow rate when not transporting a droplet of sample and immediately prior to applying the acoustic energy to the quantity of sample, the second flow rate preferably being greater than the first flow rate. The first flow rate may be greater than the second flow rate in some embodiments, but preferably the second flow rate is greater than the first flow rate. The application of the second flow rate gas stream advantageously purges the volume in the region around the quantity of sample of residual gases prior to droplet ejection. Droplet ejection is initiated by the application of a first magnitude of acoustic energy. Whilst this purging is being performed a second magnitude of acoustic energy may be applied, the second magnitude being lower than the first magnitude, so as to determine properties of the quantity of sample, such as, for example, the distance between the acoustic transducer and the free surface of the quantity of sample, which is of use for adjustment of the focus of the acoustic energy subsequently applied. Hence preferably the gas stream is supplied at a first flow rate whilst transporting the droplet of sample, and the gas stream is supplied at a second flow rate when not transporting a droplet of sample and whilst a second magnitude of acoustic energy is being applied to determine the properties of the quantity of sample immediately prior to applying a first magnitude of acoustic energy that results in droplets being ejected from the quantity of sample, the second flow rate being greater than the first flow rate.

Preferably the gas stream is supplied so as to form a gas curtain which at least partially surrounds the quantity of sample and/or partially surrounds the droplet of sample as it leaves the surface of the quantity of sample, the term gas curtain being herein used to mean a partial or complete sheath of gas. Apparatus embodying the invention comprises a gas conduit arranged between the gas supply and the sample support and between the sample support and an inlet of the analysis device. Preferably the gas conduit comprises a first gas conduit arranged between the gas supply and the sample support and a second gas conduit arranged between the sample support and an inlet of the analysis device. Where the quantity of sample is located on the solid surface of the sample support in the form of a liquid drop, preferably the first gas conduit is configured to provide gas to the first surface of the sample support, and the gas stream passes through a portion of the sample support in one or more channels, the channels extending from the first surface through to the second surface of the sample support, the quantity of sample being located upon the second surface of the sample support (the first and second surfaces of the sample support having been described above). In a preferred embodiment where the quantity of sample is located on the solid surface of the sample support within a containment vessel and the second side of the sample support is inside the containment vessel and is the inside lower surface of the containment vessel, preferably the gas stream passes through a portion of the sample support in one or more channels. In some embodiments, the channels extend from the first surface and within one or more side walls of the containment vessel to a third surface, the third surface being a greater distance from the first surface than the is the quantity of sample, e.g. the third surface may form the rim of the containment vessel. In other embodiments, the channels pass into the sample support through a surface and extend within the sample support to the third surface. Where the containment vessel is a well within a well plate, the third surface is preferably part of the upper surface of the well plate, as will be further described. Where a gas curtain at least partially surrounds the quantity of sample and the quantity of sample is located on an inside lower surface of a containment vessel, the gas curtain partially surrounds the quantity of sample whilst the gas travels within one or more channels formed within one or more side walls of the containment vessel. Preferably the curtain of gas is primarily directed normal to and away from the side of the solid surface upon which the quantity of sample is located. Preferably the gas conduit supplies the stream of gas in the form of a gas curtain at least partially surrounding a volume adjacent the sample support site so as to partially surround the droplet of sample as it leaves the surface of the quantity of sample on the sample support site.

In preferred embodiments the acoustic transducer applies acoustic energy to the quantity of sample through the solid surface of the sample support. Preferably the acoustic transducer applies acoustic energy to the quantity of sample through the first surface of the sample support and out of the second surface of the sample support, the first and second surfaces having being described above. It is preferable that at least a portion of the first and second surfaces are substantially parallel so that the path length through the sample support along the path of the acoustic energy is substantially the same for all beams of acoustic energy. In one preferred embodiment the acoustic transducer is located within the first gas conduit, as will be further described.

Apparatus embodying the invention comprises a gas conduit arranged between the gas supply and the sample support and between the sample support and an inlet of the analysis device. Preferably the gas conduit comprises a first gas conduit arranged between the gas supply and the sample support and a second gas conduit arranged between the sample support and an inlet of the analysis device. Preferably the second gas conduit comprises a carrier tube and the carrier tube accepts at least some of the gas which is, in use, delivered by the first conduit. More preferably the carrier tube accepts substantially all the gas which is, in use, delivered by the first conduit. The gas conduit serves to at least partially constrain the gas stream as it travels from the sample support to the analysis device, and thereby constrain part or the entire transport path of the ejected droplet. In preferred embodiments, the second gas conduit comprising the carrier tube serves to at least partially constrain the gas stream as it travels from the sample support to the analysis device, and thereby constrain part or the entire transport path of the ejected droplet.

In preferred embodiments the first gas conduit is sealed to a surface of the sample support with a gas-tight seal, so as to surround the one or more channels where they emerge on the sample support and the second gas conduit is sealed to another surface of the sample support with a gas-tight seal, so as to surround the one or more channels where they emerge on the other surface of the sample support. The one or more gas tight seals may be accomplished by an o-ring elastomer seal, and/or the relevant surface of the sample support may itself comprise compressible material.

Where the quantity of sample is located on the solid surface of the sample support in the form of a liquid drop, preferably an inlet of the second gas conduit (which may comprise a carrier tube) is placed in contact with a portion the solid surface of the sample support upon which the quantity of sample is located, and the second gas conduit at least partially surrounds the quantity of sample and at least partially surrounds one or more channels, the channels extending from the first side through to the second side of the solid surface, the quantity of sample being located upon the second side of the solid surface. More preferably the inlet of the second gas conduit is in contact with and forms a gas tight seal with the solid surface upon which the quantity of sample is located, and the second gas conduit at least partially surrounds the quantity of sample and at least partially surrounds one or more channels, the channels extending from the first side through to the second side of the solid surface, the quantity of sample being located upon the second side of the solid surface. Alternatively, the sample support may comprise a protuberance such as a small rod, in which case either: a single gas conduit is used and the gas conduit at least partially surrounds the protuberance; or the first gas conduit or the second gas conduit at least partially surrounds the protuberance, and an outlet of the first gas conduit is at least partially connected to an inlet of the second gas conduit.

Where the quantity of sample is located on the solid surface of a sample support within a containment vessel and the second surface of the sample support is inside the containment vessel and is the inside lower surface of the containment vessel, preferably the second gas conduit (which may comprise a carrier tube) at least partially surrounds and more preferably fully surrounds one or more channels where they emerge on the third surface of the sample support, the channels extending from the first surface of the sample support through to a third surface of the sample support as described above. In another preferred embodiment, the channels extend from one location on the third surface to another location on the third surface, as will be further described. Where this third surface of the sample support comprises a rim, the inlet of the second gas conduit preferably also abuts the rim, more preferably with a gastight seal, so as to surround the one or more channels as they emerge on the third surface. The gas tight seal may be accomplished by an o-ring elastomer seal, and/or the surface of the sample support may itself comprise compressible material.

An alternative arrangement for supplying the stream of gas through a gas conduit comprises a first gas conduit coupled to the gas supply and coupled to the sample support, and a second gas conduit being coupled to the sample support and the inlet of the analysis device, wherein the first gas conduit supplies gas into a first set of one or more channels in the sample support and the second gas conduit receives gas from a second set of one or more channels in the sample support, the first set of one or more channels being in gaseous communication with the second set of one or more channels. Preferably both the first set of one or more channels and the second set of one or more channels are accessible from the same surface of the sample support and most preferably this surface is the third surface of the sample support as described above, in which case the acoustic transducer is not contained within the first gas conduit. In this case, the gas conduit supplies the stream of gas in the form of a gas curtain at least partially surrounding a volume adjacent the sample support site so as to partially surround the droplet of sample as it leaves the surface of the quantity of sample on the sample support site. An example of such an embodiment is given below.

The gas conduit extending from the region of the sample to the analysis device may extend in a straight line (i.e. the axis of the gas conduit extends in a straight line), or it may extend so as to incorporate one or more changes of direction (e.g. it may extend along a curved path). Preferably the path is such that the droplet of sample does not contact any solid surface along the transport path after leaving the quantity of sample and before entering the analysis device, and depending upon the diameter of the gas conduit (amongst other conditions), this may limit the minimum radius of curvature of any curved section, for example. Preferably the gas conduit extends axially a distance between 10 and 100 mm from the region of the sample to the analysis device. In some embodiments the gas conduit may be longer than this, extending between 100 and 1000 mm. Where an ejected droplet size is too large for efficient direct injection into the analysis device, a droplet modifier may be incorporated into the transport path, as described below, in which case the second conduit or carrier tube may incorporate such a droplet modifier in the arrangement between the sample support and the inlet of the analysis device.

The gas conduit extending from the region of the sample to the analysis device may have different cross sectional shapes (the cross section being normal to the tube axis). Preferably the gas conduit cross section is substantially circular. Preferably the internal cross sectional area reduces somewhat (i.e. the conduit narrows in at least one dimension) as the gas conduit extends away from the sample support, in order to increase the flow velocity of the gas in a region above the surface of the quantity of liquid sample.

Preferably the gas stream enters the analysis device as it enters a sample inlet. Preferably an outlet of the gas conduit is directly connected to the inlet of the analysis device. More preferably the gas conduit forms a single component with the inlet of the analysis device so that there are no discrete step changes in the gas flow resistance which may increase the risk of droplets contacting a solid surface. Where the outlet of the gas conduit is directly connected to the inlet of the analysis device, preferably the internal cross sectional area of the inlet of the analysis device is larger than the internal cross sectional area of the outlet of the gas conduit. Preferably the droplet of sample entrained in the gas stream enters the analysis device and material within the entrained droplet of sample is excited or ionized within the analysis device without having come into contact with any solid surface on its journey from the quantity of sample.

The analysis device is preferably one of: an Atomic Absorption Spectrometer, an Inductively Coupled Plasma Optical Emission Spectrometer, an Inductively Coupled Plasma Mass Spectrometer, a Microwave Induced Plasma Optical Emission Spectrometer, a Microwave Induced Plasma Mass Spectrometer, an Atomic Fluorescence Spectrometer, a Laser Enhanced Ionization Spectrometer. The invention is highly suitable for application with either an Inductively Coupled Plasma Optical Emission Spectrometer or an Inductively Coupled Plasma Mass Spectrometer. Most preferably the analysis device is an Inductively Coupled Plasma Optical Emission Spectrometer.

Alternatively, the analysis device may be a time-of-flight mass spectrometer utilizing a desolvation membrane such as a Nafion™ tube, and an ionization device such as a corona discharge, a photo-ionization source, or a radioactive ionizing source such as $^{63}$Ni foil, $^{241}$Am or tritium ($^{3}$H). The analysis device may also be an ion mobility analyser, utilizing a desolvation membrane such as a Nafion™ tube. Other types of analysis device suitable for use with the invention are envisaged.

The inlet of the analysis device preferably comprises the inlet to the injector tube of a torch, where the analysis device utilizes a torch (such as in, for example, an ICP-OES or ICP-MS). Where the analysis device is an atomic absorption spectrometer the inlet of the analysis device comprises the inlet to the burner. Where the analysis device is an atomic fluorescence spectrometer, the inlet to the analysis device comprises an inlet to the optical cell.

The droplet may be of any size suitable for the analysis device. Preferably the droplet size lies in the range 0.1 to 10 μm in diameter. Droplets of this size are suitable for highly efficient direct injection into an inductively coupled plasma, for example. Alternatively the droplet diameter may be 10 to 200 μm. Droplets of this size may be advantageous where a higher sample flow rate is required and a limited acoustic energy repetition rate is available.

Larger droplets may require a droplet modifier located between the quantity of sample and the analysis device and in the transport path of the droplet of sample as it is transported using the gas stream, the droplet modifier being configured to remove solvent from the droplet. Preferably solvent is removed from the droplet by evaporation using a heated gas, an optical heater, convective heater, microwave heater, R.F. heater, or a broadband I.R. source, e.g., LED, laser, electrically excited filament; or a narrowband I.R. source e.g., LED or a laser. Accordingly, the droplet modifier preferably comprises one or more of the aforementioned means (supply of heated gas, an optical heater etc.). When using a narrowband source the source will preferably emit at a wavelength that is matched to an absorbance frequency of the sample.

Preferably the acoustic energy is repeatedly applied to the quantity of sample so as to produce a stream of droplets from one quantity of liquid sample for a period of time. Preferably the acoustic transducer is controlled by a computer.

In preferred embodiments the sample support comprises a well plate, each well having an internal capacity of between 5 μl and 2 ml. Preferably the well plate contains a plurality of wells. Where the sample support comprises a plurality of sample support sites, such as containment vessels, indentations, protuberances, or sites having undergone surface treatment such as etching or impregnation, preferably the relative positions of the sample support and the acoustic transducer are periodically changed so as to position a different quantity of sample in the path of acoustic energy emitted by the acoustic transducer. In preferred embodiments the sample support is moved relative to the acoustic transducer so that acoustic energy may be sequentially applied to some or all the sample support sites included in the sample support. Preferably the relative movement of the sample support and the acoustic transducer is accomplished using automated means and is controlled by a computer. The gas conduit is preferably also moved relative to the sample support, preferably by automated means, so that the gas conduit may deliver gas to and from different sample support sites. Both the acoustic transducer and the gas conduit are preferably moved in directions perpendicular to the sample support using linear actuators. Various such actuators are known in the art. Once the acoustic transducer and gas conduit have been moved away from the sample support, the sample support may be repositioned and the acoustic transducer and gas conduit may then be reapplied to the sample support so that sample may be emitted from a new sample support site and transported in the gas stream to the analysis device. Where the sample support comprises an array of sample support sites arranged in a circle, advantageously the sample support may simply be rotated in order to position a different sample support site into the path of the acoustic transducer and in the path of the gas conduit.

Identification of different sample support sites may be accomplished by known means, such as barcodes or RFID recognition, so that different samples may be tracked and different types of sample support arrangements may be identified.

Advantageously, the gas conduit, acoustic droplet generator, sample support plate and inlet of the analysis device may be contained within an enclosure filled with inert gas such as argon, so that samples located on the sample support are not exposed to ambient air. Alternatively, where samples are contained within vessels, each vessel may be covered by a film of a polymer to protect the samples from ambient air, and during the process of locating the second gas conduit onto the sample support adjacent a sample support site the polymer film seal may be broken to provide a path for emitted droplets from the sample support site.

Quantities of sample may be introduced onto or into the one or more sample support sites manually or by automated means. Quantities of different samples may be located on different sample support sites. Where there are multiple sample support sites, the quantities of sample or samples are preferably introduced onto or into multiple sample support sites simultaneously by automated means. Automated means include pumps as are known in the art, or by any other means.

Two different liquids may be introduced to an analysis device for simultaneous analysis using a method comprising the steps of: using a first droplet-on-demand generator to provide a first stream of droplets of a first liquid; using a second droplet-on-demand generator to provide a second stream of droplets of a second liquid and combining the first and second streams of droplets before they enter the analysis device. The method may be performed using a sample introduction system for an analysis device comprising a first droplet-on-demand generator suitable for generating a stream of droplets from a first liquid; a second droplet-on-demand generator suitable for generating a stream of droplets from a second liquid; a gas supply arranged to supply a first stream of gas to entrain droplets generated from the first liquid; a gas supply arranged to supply a second stream of gas to entrain droplets generated from the second liquid; and a gas conduit upstream of an inlet of the analysis device arranged to combine the first and second streams of gas before they enter the analysis device.

A droplet-on-demand droplet generator is a type of droplet generator in which the droplet generation apparatus enables a single droplet to be ejected in response to a control signal. The invention may be applied to various known and as-yet unknown droplet-on-demand generators. Preferably the droplet-on-demand generator comprises one of a piezo-actuated droplet generator, a thermal inkjet device, a monodisperse dried microparticulate injector, an acoustic transducer (e.g. configured in a sample introduction system according to the further aspect independent of the invention described herein).

Where there are multiple sample support sites, preferably some of the sample support sites may be sites for the location of quantities of diluent and some may be sites for the location of quantities of one or more standards. The provision of more than one droplet-on-demand generator, which preferably comprises an acoustic transducer, may then be used for substantially simultaneous emission of a stream of droplets of sample from a first site, and a stream of droplets of a diluent and/or one or more standards from one or more other sites. Preferably the first and second streams of droplets are combined in a gas stream and the gas stream transports the droplets to the inlet of the analysis device. Preferably each site upon the sample support is provided with a gas stream, and the gas streams are combined prior to them reaching the analysis device, thereby mixing the streams of droplets prior to reaching the analysis device, the streams of droplets consisting of different constituents from the different sites, the different constituents being delivered to the analysis device simultaneously. Preferably the gas stream or gas streams comprise inert gas and more preferably substantially only inert gas. Preferably the inert gas comprises argon. Advantageously the effective mixing occurs whilst the droplets are in flight and are not in contact with any surfaces. Hence, preferably a plurality of droplets is created substantially simultaneously from a plurality of quantities of liquid each located on a solid surface and wherein at least one quantity of liquid comprises sample and one quantity of liquid comprises diluent and/or a standard. The droplets of sample are transported into the analysis device using a gas stream, and the gas stream comprises a first gas stream, and a second gas stream is combined with the first gas stream, the second gas stream containing droplets of diluent or droplets of a standard. Where the sample is dispensed using a droplet-on-demand generator comprising an acoustic transducer, the sample advantageously does not come into contact with any solid surface other than the surface of the sample support and hence there is no wash-out required between the analysis of different samples, as the different samples are located upon different sample support sites. In this case, the second droplet-on-demand generator may be of any type, as it is only dispensing a single solution containing diluent and/or standard to be combined with different samples.

In cases where a low droplet admission rate into the analysis device is required, the droplet stream may be diluted by the addition of an additional gas downstream of the sample support. Dilution is in this case a reduction in the droplet density in the gas stream entering the analysis device, and it is achieved by adding an additional gas stream into the gas stream in which the droplets are entrained. The additional gas may be of the same or similar composition to the gas stream in which the droplets are entrained, or it may be a different gas. The additional gas may also serve to increase the gas flow rate into the analytical device where that device requires a higher gas flow rate than is desirable to entrain the droplets. Hence there is a method of introducing liquid sample into an analysis device as previously described wherein the gas stream comprises a first gas stream, and a second gas stream is combined with the first gas stream upstream of the analysis device.

Advantageously, the present invention provides for supplying acoustically emitted droplets to an analysis device by entraining the droplets in a gas stream. In prior art systems, acoustic droplet generators have been used to emit droplets from a quantity of sample and to deposit them onto another surface in relatively close proximity to the acoustic transducer. In the present invention the gas stream advantageously transports the droplets into the analysis device directly. Preferably the droplets are transported into the analysis device without having come into contact with any surface once they leave the surface of the quantity of liquid sample. The use of an acoustic droplet generator with an analysis device enables droplets to be supplied to the analysis device without the use of tubing to transfer sample-containing liquid from a storage vessel to the droplet generator and wherein the droplet generator itself does not present exposed surfaces to the sample-containing liquid. There is therefore no requirement to wash out tubing or surfaces of the droplet generator in between the uptake of different samples, and throughput of samples to the analysis device is greatly increased.

Other advantages provided include the mixing of sample with diluent and/or standards within the gas flow entering the inlet of the analysis device, without the requirement for any mixing vessel, the surfaces of which would otherwise require cleaning before another sample could be admitted. Mixing occurs within the gas stream without further intervention, and so no additional mixing devices are required, reducing complexity.

DESCRIPTION OF THE DRAWINGS

FIG. 1 is a schematic diagram of a prior art droplet ejection system utilizing an acoustic droplet ejector.

FIG. 2 is a schematic diagram of a prior art sample introduction system for sample analysis using an analysis device.

FIGS. 3A-3C are schematic diagrams of embodiments of the present invention, FIG. 3A is a schematic diagram of the top-view of a well plate. FIG. 3B is a schematic cross sectional diagram of the well plate of FIG. 3A in the section marked A-A. FIG. 3C is the schematic cross sectional diagram of the well plate of FIG. 3B with additional components shown.

FIG. 4 is a schematic cross-sectional diagram of another embodiment of the present invention.

FIG. 5 is a schematic cross-sectional diagram of yet another embodiment of the invention.

DETAILED DESCRIPTION

FIG. 1 is a schematic diagram of a prior art droplet ejection system utilizing an acoustic droplet ejector. Liquids to be dispensed, 10, are contained within an array of sample vessels, 20, in this case a well-plate. An acoustic transducer and lens system, 30, provides pulsed acoustic energy, 40, which travels from the acoustic transducer, 32, and through the incorporated lens system, 34, before being emitted to pass through the well-plate, 20, and into one of the vessels, 22. The lens system, 34, incorporated into the transducer and lens system 30 is arranged to focus the acoustic pulse on the surface region, 12, of the liquid within the vessel, 22. Upon arrival at the surface region, 12, the acoustic energy, 40, disrupts the surface of the liquid so as to eject a droplet, 14, of the liquid, 10. The droplet, 14 (not to scale), leaves the surface region, 12, and travels upward, approximately orthogonally away from the surface region 12, and is deposited on receiving plate 50, within one of the wells therein. By this means liquids may be transferred droplet by droplet from a sample vessel, 22 to a receiving plate, 50. The relative positions of the acoustic transducer and lens system, 30, the array of sample vessels, 20, and the receiving plate, 50, may be varied, so that sample liquids within different vessels in the array 20 may receive focused acoustic energy and the emitted droplets may be collected at different places upon receiving plate 50. Preferably the relative positions are determined using automated means. Different liquid levels within different sample vessels in array 20 may require variation of the focusing of the lens system 34 in order to ensure acoustic energy is focused in the surface regions of the respective liquids. Methods have been devised to measure the liquid level within such vessels using acoustic energy reflected from the liquid surface and such information can be used to continually vary the focusing properties of the lens system 34 in an automated manner.

FIG. 2 is a schematic diagram of a prior art sample introduction system for sample analysis using an inductively coupled plasma mass spectrometer (ICP-MS) as the analysis device. FIG. 2 shows a nebulizer, 60, having sample inlet tube 62 and gas inlet tube 64. Typically nebuilser 60 is made of glass. In use, a stream of liquid sample (not shown) is supplied into inlet tube 62, whilst an inert gas, usually argon, is supplied into gas inlet tube 64. The inert gas has sufficient flow velocity as it exits from the tip of the nebulizer 66 to cause a local drop in pressure which acts to draw liquid sample from the narrowed sample inlet tube 68 and to break the liquid emerging from tube 68 into droplets 69. A large range of droplets sizes is produced by such nebulizers. The gas flow from the nebulizer 60 emerges into spray chamber 70, which in this example is an impact-bead spray chamber having impact bead 72. Spray chamber 70 is typically made of glass or an inert polymer. The sample droplets 69 are entrained in the gas stream and many droplets are caused to strike impact bead 72, whilst a proportion flow around impact bead 72. Droplets which strike impact bead 72 are predominantly the larger droplets, and by this means impact bead 72 serves to filter out larger droplets, the liquid within such droplets flowing down impact bead 72 and flowing to waste through waste outlet 74. As already noted, with pneumatic nebuilsers of the type described, only 1-2% of the droplets produced are of a size useful for analysis. Smaller droplets which flow around impact bead 72 are carried by the gas stream to outlet 76 and enter the inlet of torch 80. Torch 80 comprises injector tube 82, auxiliary tube 84 and outer tube 86. Typically torch 80 is made of quartz glass or ceramic elements. The gas flow entering injector tube 82 is known as an injection gas. Additional gas is supplied to auxiliary tube 84 via inlet 85, and this gas flow is known as auxiliary gas. A further gas flow is supplied to outer tube 86 via inlet 87, and this gas flow is known as the cool gas, as it is predominantly used to introduce a barrier of gas along the inside surface of outer tube 86. ICP coil 90 is used to couple RF power (typically, at 27 MHz) into a plasma formed within outer tube 86 in the region 88 (plasma is not shown). Droplets entering the inlet of torch 80 via injector tube 82 are transported in the injector gas into the axial region of the plasma 91 whereupon they desolvate and atomise and a proportion of the atoms liberated are ionized. Sample products passing through the plasma enter sample cone 92 through orifice 94, and pass into the inlet system of the mass spectrometer (not shown).

Figure 2:
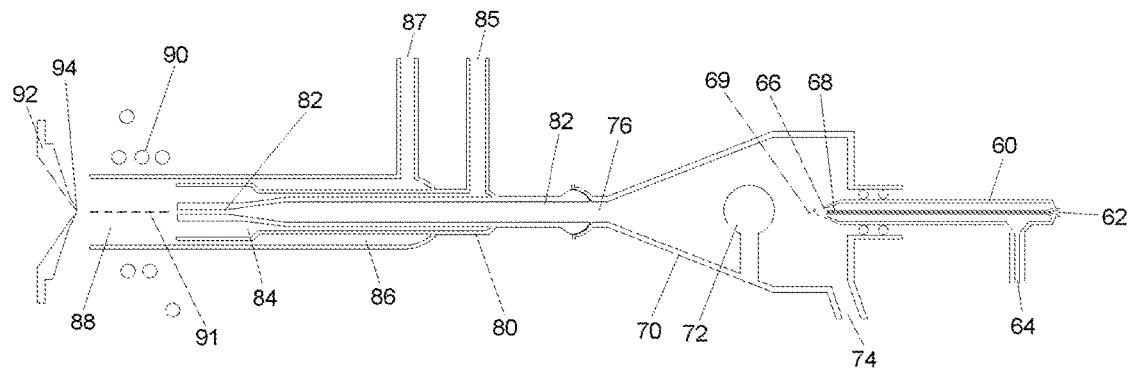

The nebulizer 60, spray chamber 70 and torch 80 of FIG. 2 may alternatively be used with an ICP-OES analysis device. Similar torch arrangements are used in MIP spectrometry; AA and AFS use somewhat differently designed torches.

Figure 3A:
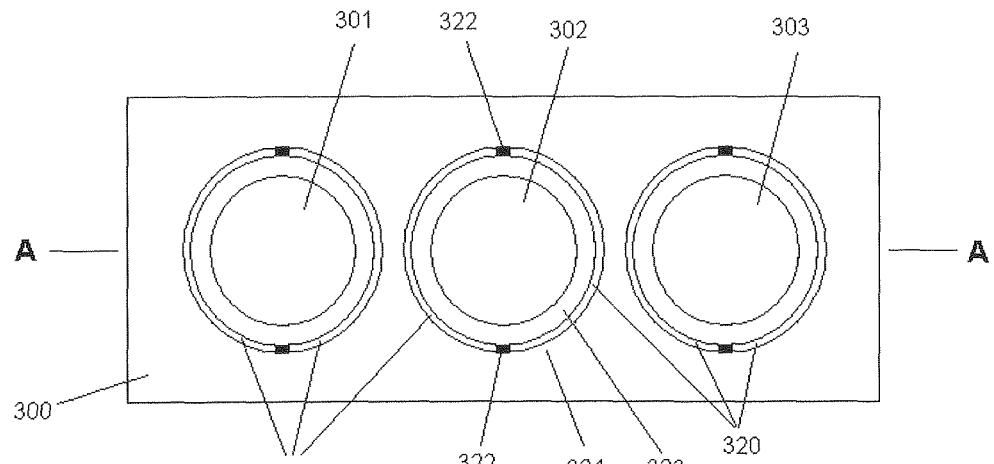
Figure 3B:
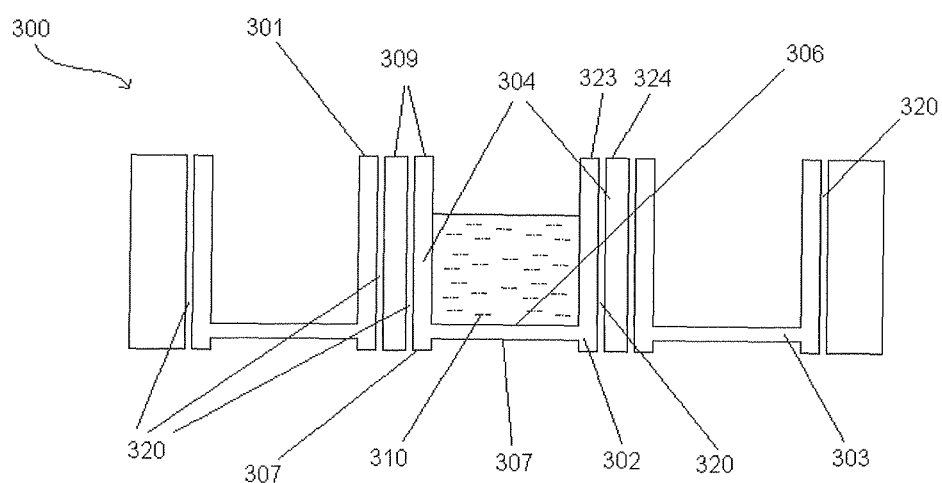
Figure 3C:
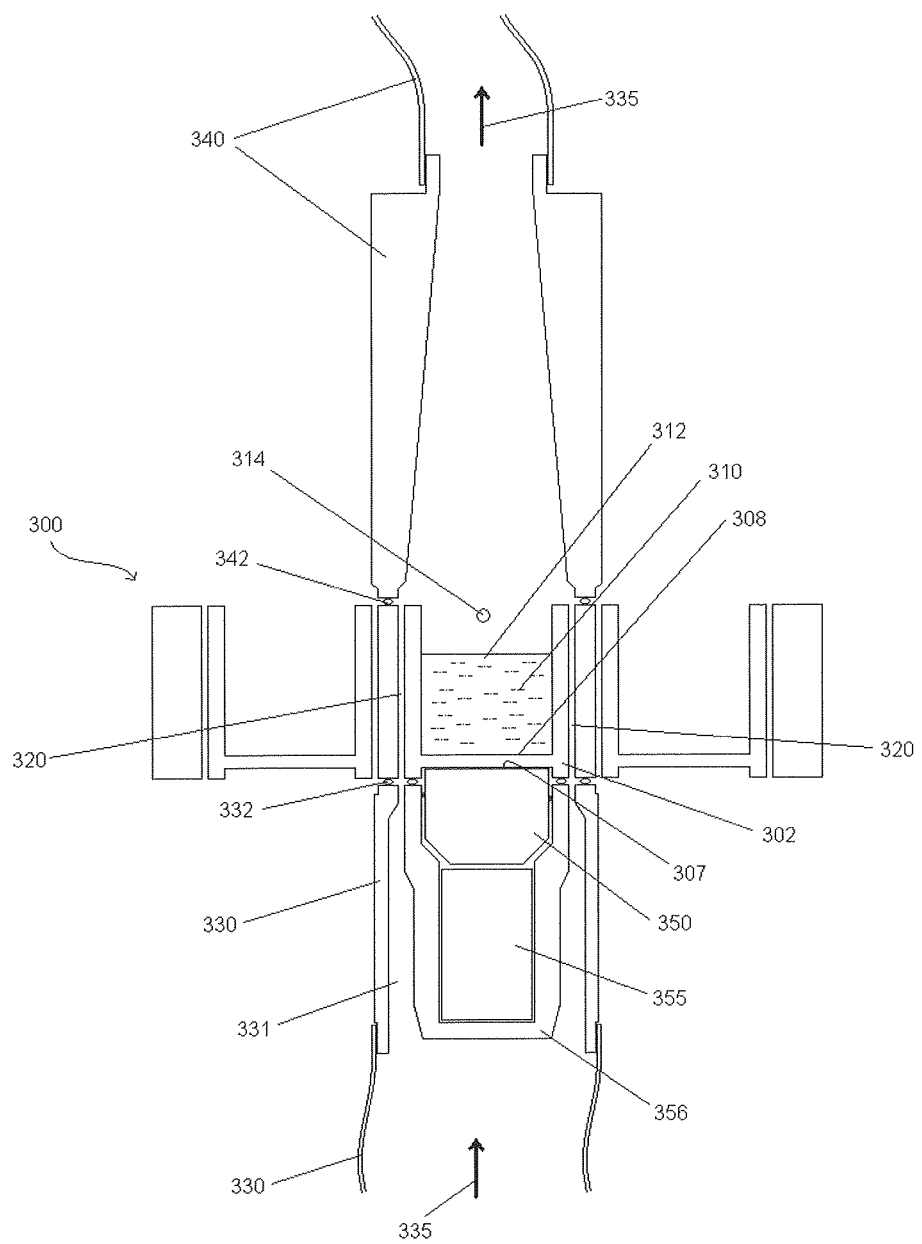

FIGS. 3A-3C are schematic diagrams of embodiments of the present invention. FIG. 3A is a schematic diagram of the top-view of a well plate. FIG. 3B is a schematic cross sectional diagram of the well plate of FIG. 3A in the section marked A-A. FIG. 3C is the schematic cross sectional diagram of the well plate of FIG. 3B with additional components shown. Well plate 300 is depicted in FIGS. 3A-3C, comprising three wells, 301, 302, 303, each well comprising a sample support site; hence there are depicted three sample support sites and the well plate 300 contains a plurality of wells. Well 302 comprises side wall 304, and well 302 has inside lower surface 306 upon which a quantity of liquid sample 310 is located (quantity of sample 310 cannot be seen in FIG. 3A). The quantity of liquid sample 310 partially fills well 302 and completely covers the inside lower surface 306; hence a solid surface of a sample support comprises inside lower surface 306 of well 302 in this example (i.e. the inside lower surface 306 is a sample support site).

Well plate 300 further comprises channels 320 which partially surround wells 301, 302, 303. With reference to well 302, channels 320 extend from a first surface 307 and within one or more side walls 304 of well 302 to a third surface 309, surface 309 being a greater distance from the first surface 307 than is the quantity of sample 310, the third surface 309 forming the rim of well 302. First surface 307 may include portions of curved surface, and may include flat surfaces with changes of direction as shown in FIG. 3B. Channels 320 do not completely surround the rim of well 302 as supporting ribs 322 are provided (shown in FIG. 3A), attaching the inner wall portion 323 of well 302 to an outer wall portion 324 of well 302. In this example the supporting ribs 322 extend from third surface 309 to first surface 307, providing a rigid attachment between portions 323 and 324. In other embodiments supporting ribs may only extend part of the way from third surface 309 towards first surface 307 and there may be more supporting ribs to achieve a similar degree of rigidity.

FIG. 3C shows acoustic transducer 350 which is arranged so that, in use, acoustic energy is emitted towards the first surface 307 of the sample support of well 302 and the quantity of liquid sample 310 is located upon a second surface 308 of the sample support. In this example second surface 308 of the sample support is the same surface as inside lower surface 306 and surface 308 forms the solid surface upon which the quantity of sample 310 is located. A portion of the first surface 307 and the second surface 308 of the sample support are substantially parallel to one another. Acoustic energy is emitted from acoustic transducer 350 towards the solid surface upon which the quantity of sample 310 is located, the acoustic energy passing through the first surface 307 of the sample support and out of the second surface 308 of the sample support.

A gas supply (not shown) is arranged to supply a stream of gas 335 to a first gas conduit 330, the first gas conduit 330 arranged between the gas supply and the sample support, A second gas conduit 340 is arranged between the sample support (well 302) and an inlet of an analysis device (not shown). Hence in this example the gas conduit arranged between the gas supply and the sample support and between the sample support and an inlet of the analysis device comprises a first gas conduit 330 and a second gas conduit 340. The inlet of the second gas conduit 340 abuts the rim of well 302 and surrounds channels 320 as they emerge on the third surface 309. The stream of gas 335 travels along gas first gas conduit 330 to the first surface 307 of the sample support and flows into and through channels 320, emerging from channels 320 into second gas conduit 340 whereupon the gas stream travels to the inlet of the analysis device. Hence the gas stream is supplied so as to form a gas curtain which at least partially surrounds the quantity of sample 310 whilst the gas travels within channels 320 formed within side walls 304 of the well 302. The curtain of gas is primarily directed normal to and away from the side of the solid surface 308 upon which the quantity of sample 310 is located. As shown in FIG. 3C the acoustic transducer 350 is located within the first gas conduit 330, along with acoustic transducer drive electronics 355 within a case 356. Electrical connections to acoustic transducer drive electronics 355 are not shown in the figure, but pass through the wall of first gas conduit 330 to a controller which comprises a computer (also not shown). The gas stream passes around case 356 which contains acoustic transducer drive electronics 355 and acoustic transducer 350, within an annular channel 331.

Acoustic energy is focused upon the surface region 312 of liquid sample 310 (shown in FIG. 3C). The acoustic energy is focused using a lens system (not shown) which is incorporated with the transducer 350, the lens system being arranged to focus an acoustic pulse emitted by transducer 350 onto the surface region 312 of the liquid sample 310 within the well 302, the acoustic pulse passing through the lower surface 306 of well 302. Upon arrival at the surface region 312, the acoustic energy (not shown) disrupts the surface of the liquid so as to eject a droplet, 314, of the liquid sample 310 (droplet 314 is not shown to scale). The droplet, 314, leaves the surface region, 312, and travels upward, approximately orthogonally away from the surface of the liquid sample 310 and passes into the second gas conduit 340, whereupon the droplet becomes entrained in the gas stream flowing in the second gas conduit 340 (as described above) and the droplet of sample is transported into the analysis device using the gas stream. The cross sectional shape of the second gas conduit 340 is substantially circular. The internal cross sectional area of the second gas conduit 340 reduces somewhat (i.e. the tube narrows) as the second gas conduit extends away from the sample support, in order to increase the flow velocity of the gas in a region above the surface of the quantity of liquid sample 310.

The first gas conduit 330 is sealed to first surface 307 of the sample support with a gas-tight seal using elastomer 332 and the second gas conduit 340 is sealed to third surface 309 of the sample support with a gas-tight seal using elastomer 342. The second gas conduit 340 serves to constrain the gas stream as it travels from the sample support to the analysis device, and thereby constrain the transport path of the ejected droplet. The second gas conduit extends 75 mm from the sample support to the inlet of an ICP-OES analysis device and contains no abrupt changes of direction so that the droplet of sample does not contact any solid surface along the transport path after leaving the quantity of sample and before entering the analysis device. In this example the droplet diameter is 5 µm and the droplet is highly suitable for direct injection into the inlet of the torch of the ICP-OES spectrometer, whereupon it may be desolvated, atomized and excited with high efficiency.

In the embodiments of FIGS. 3A-3C, the wells 301, 302, 303 have internal capacity of 500 ul and the well plate 300 is formed from polypropylene. The gas supply comprises argon gas, the gas flow rate being 0.5 $l \cdot min^{-1}$ at a pressure of 1.5-1.8 atm, the gas temperature being 20-25 degrees C. The average gas velocity in the second gas conduit is 1.2-1.5 $m \cdot s^{-1}$. These working parameters are suitable for aqueous samples such as drinking water for analysis in an ICP-OES analysis device.

The acoustic transducer 350 is controlled so as to repeatedly emit pulses of acoustic radiation of a first magnitude of acoustic energy towards the surface region 312 of the quantity of liquid sample 310, thereby repeatedly emitting droplets for entrainment in the gas stream. Periodically during this process, and before the first pulse of acoustic radiation of a first magnitude of acoustic energy is applied to a fresh quantity of liquid sample, a pulse of a second magnitude of acoustic energy is radiated, the second magnitude being lower than the first magnitude. This second magnitude pulse is used to determine the distance between the acoustic transducer 350 and the surface region 312 of the quantity of sample 310. This is achieved as transducer 350 also comprises a detector for detecting reflected acoustic energy. By measuring the time period between the emitted pulse of acoustic energy and the detection of the reflected pulse of acoustic energy the effective path length between the transducer 350 and the surface region 312 of the quantity of liquid sample 310 may be determined, and this information is used to adjust parameters controlling the lens which focuses the acoustic radiation of a first magnitude which is subsequently applied. This process is periodically utilized during a sequence of pulses of acoustic radiation of a first magnitude of acoustic energy so that the location of the surface region 312 of the diminishing quantity of liquid sample 310 may be correctly determined.

Quantities of different samples are located within wells 310, 302 and 303. The relative positions of the sample support (the well plate 300) and the acoustic transducer 350 are periodically changed so as to position a different quantity of sample in the path of acoustic energy emitted by the acoustic transducer 350. The sample support is moved relative to the acoustic transducer so that acoustic energy may be sequentially applied to each of wells 301, 302 and 303 in well plate 300. By moving the sample support and keeping the transducer 350 at the same position relative to the inlet of the analysis device, the path of second gas conduit 340 remains fixed and it can be ensured that the droplets do not come in contact with any solid surface between leaving the quantity of sample and entering the analysis device. The relative movement of the sample support 300 and the acoustic transducer 350 is accomplished using automated means and is controlled by a computer. The first and second gas conduits 330,340 are moved by linear actuators (not shown) orthogonally to first surface 307 and third surface 309 respectively to disengage from the well plate 300, enabling well plate 300 to be moved so that first and second gas conduits 330, 340 may be re-engaged with well plate 300 aligned with a different well. Acoustic transducer 350, acoustic transducer electronics 355 and case 356 being attached to first gas conduit 330 move with first gas conduit 330.

A gas stream is supplied at a first flow rate whilst transporting the droplet of sample 314 from the quantity of liquid sample 310 to the analysis device, and a gas stream is supplied at a second flow rate when not transporting a droplet of sample and immediately prior to applying the acoustic energy to the quantity of sample, the second flow rate being greater than the first flow rate. The application of the second gas stream advantageously purges the volume in the region around the quantity of sample of residual gases prior to droplet ejection, and this application of the second gas stream is performed immediately after positioning a different quantity of sample in the path of acoustic energy emitted by the acoustic transducer 350 so that residual atmospheric gases included during the positioning process are not carried into the analysis device at the same time as droplets of sample.

Figure 4:
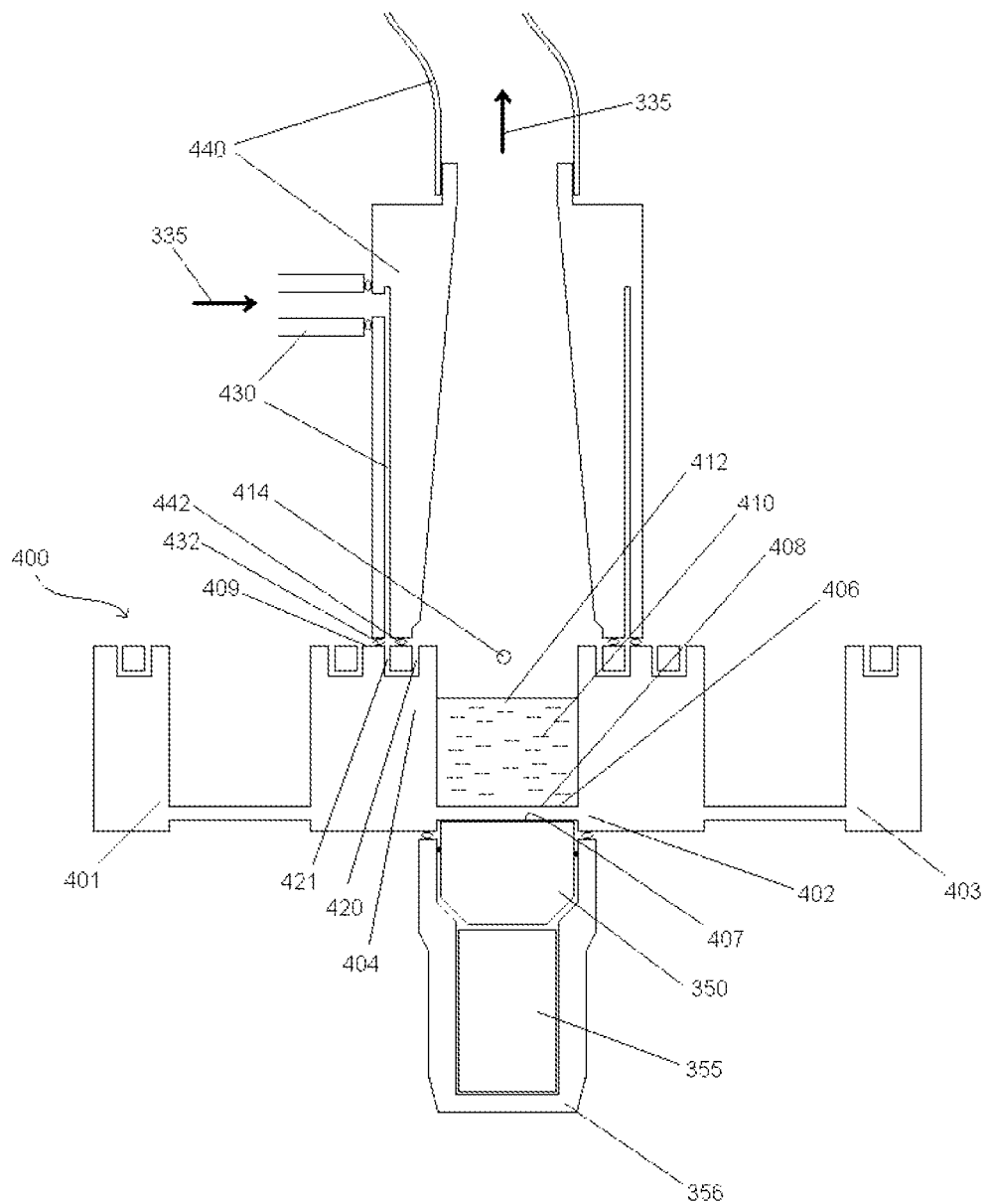

FIG. 4 is a schematic cross-sectional diagram of a further embodiment of the present invention. This embodiment shares some of the features of the previous embodiment described in relation to FIG. 3 and like components have the same identifiers. Well plate 400 is depicted in FIG. 4, comprising three wells 401, 402, 403. Well 402 comprises side wall 404, and well 402 has inside lower surface 406 upon which a quantity of liquid sample 410 is located. The quantity of liquid sample 410 partially fills well 402 and completely covers the inside lower surface 406; hence a solid surface of a sample support comprises inside lower surface 406 of well 402 in this example.

Well plate 400 further comprises channels 420, and channels 421 which connect within the well plate to channels 420. Channels 420 and channels 421 are accessible from only a single surface 409 of well plate 400, the surface being previously described as the third surface. Surface 409 comprises the rim of well 402. Channels 420 and 421 do not completely surround the rim of well 402, supporting ribs being provided (but not shown) in a similar manner to ribs 322 in FIG. 3, however both channels 420 and 421 almost completely surround the rim of well 402.

Acoustic transducer 350 is arranged in a similar manner to that described in relation to FIG. 3, so that, in use, acoustic energy is emitted towards first surface 407 of the sample support of well 402, the quantity of liquid sample 410 being located upon second surface 408 of the sample support. However in the embodiment of FIG. 4 the acoustic transducer 350, acoustic transducer drive electronics 355 and case 356 are not located within a first gas conduit, but are instead unenclosed. A portion of the first surface 407 and the second surface 408 of the sample support are substantially parallel to one another. Acoustic energy is emitted from acoustic transducer 350 towards the solid surface upon which the quantity of sample 410 is located, the acoustic energy passing through the first surface 407 of the sample support and out of the second surface 408 of the sample support. Acoustic energy is focused as described in relation to FIG. 3 and the pulse of focused acoustic energy (not shown) ejects a droplet 414 of the liquid sample from surface region 412 of the liquid sample 410.

In this embodiment a gas supply (not shown) is arranged to supply a stream of gas 335 to a first gas conduit 430, the first gas conduit 430 arranged between the gas supply and the sample support. The stream of gas 335 passes into channels 421 and then into channels 420, emerging from surface 409 into a region above the surface of the liquid sample 410, the region being within a second gas conduit 440 whereupon the gas stream travels to the inlet of the analysis device. Second gas conduit 440 is arranged between the sample support and an inlet of the analysis device (not shown). Hence the gas stream is supplied so as to form a gas curtain at least partially surrounding a volume adjacent the sample support site so as to partially surround the droplet of sample as it leaves the surface of the quantity of sample on the sample support site. The curtain of gas is primarily directed normal to and away from the side of the solid surface 408 upon which the quantity of sample 410 is located as it travels in channels 420 and in the second gas conduit 440 in the region immediately above the surface of the liquid sample 410.

The droplet, 414, leaves the surface region, 412, and travels upward, approximately orthogonally away from the surface of the liquid sample 410 and passes into the second gas conduit 440, whereupon the droplet becomes entrained in the gas stream flowing in the second gas conduit 440 and the droplet of sample is transported into the analysis device using the gas stream. The cross sectional shape of the second gas conduit 440 is substantially circular. The internal cross sectional area of the second gas conduit 440 reduces somewhat (i.e. the tube narrows) as the second gas conduit extends away from the sample support, in order to increase the flow velocity of the gas in a region above the surface of the quantity of liquid sample 410.

The first gas conduit 430 is sealed to third surface 409 of the sample support with a gas-tight seal using elastomer 432 and the second gas conduit 440 is sealed to third surface 409 of the sample support with a gas-tight seal using elastomer 442. The second gas conduit 440 serves to constrain the gas stream as it travels from the sample support to the analysis device, and thereby constrain the transport path of the ejected droplet. The second gas conduit extends 55 mm from the sample support to the inlet of an ICP-MS analysis device and contains no abrupt changes of direction so that the droplet of sample does not contact any solid surface along the transport path after leaving the quantity of sample and before entering the analysis device. In this example the droplet diameter is 5 µm and the droplet is highly suitable for direct injection into the inlet of the torch of the ICP-MS spectrometer, whereupon it may be desolvated, atomized and ionised with high efficiency.

In the embodiment of FIG. 4, the wells 401, 402, 403 have internal capacity of 500 µl and the well plate 400 is formed from polypropylene. The gas supply comprises argon gas, the gas flow rate being 0.7 l·min$^{-1}$ at a pressure of 1.5 atm, the gas temperature being 20 degrees C. The average gas velocity in the second gas conduit is 1.5 m·s$^{-1}$. These working parameters are suitable for aqueous samples such as drinking water for analysis in an ICP-MS analysis device.

The operation of the acoustic transducer is controlled in a manner similar to that described in relation to the embodiment of FIG. 3. Quantities of different samples are located in the different wells of well plate 400 and the relative motion of the acoustic transducer 350 and sample support plate 400 enables different samples to be dispensed from well plate 400. Acoustic transducer 350, acoustic transducer electronics 355 and case 356 are moved in this embodiment using a linear actuator (not shown), which has movement in a direction orthogonal to first surface 407. Gas conduits 430 and 440 are advantageously moved as one in the embodiment of FIG. 4, by a second linear actuator (not shown) which has movement in a direction orthogonal to third surface 409. By this means acoustic transducer 350, acoustic transducer electronics 355 and case 356 are disengaged from well plate 400, and first and second gas conduits 430, 440 are also disengaged from well plate 400 enabling a different well in well plate 400 to then be positioned so that acoustic transducer 350, acoustic transducer electronics 355, case 356 and gas conduits 430, 440 may engage onto the different well, and a different sample may be dispensed. Well plate 400, first and second gas conduits 430, 440, the inlet to the analysis device and case 356 containing acoustic transducer 350 and acoustic transducer electronics 355 are all maintained in a protective argon atmosphere so that during the process of positioning a different well for the dispensing of a different sample, contaminant gases are substantially excluded from all the wells and the gas conduits.

Figure 5:
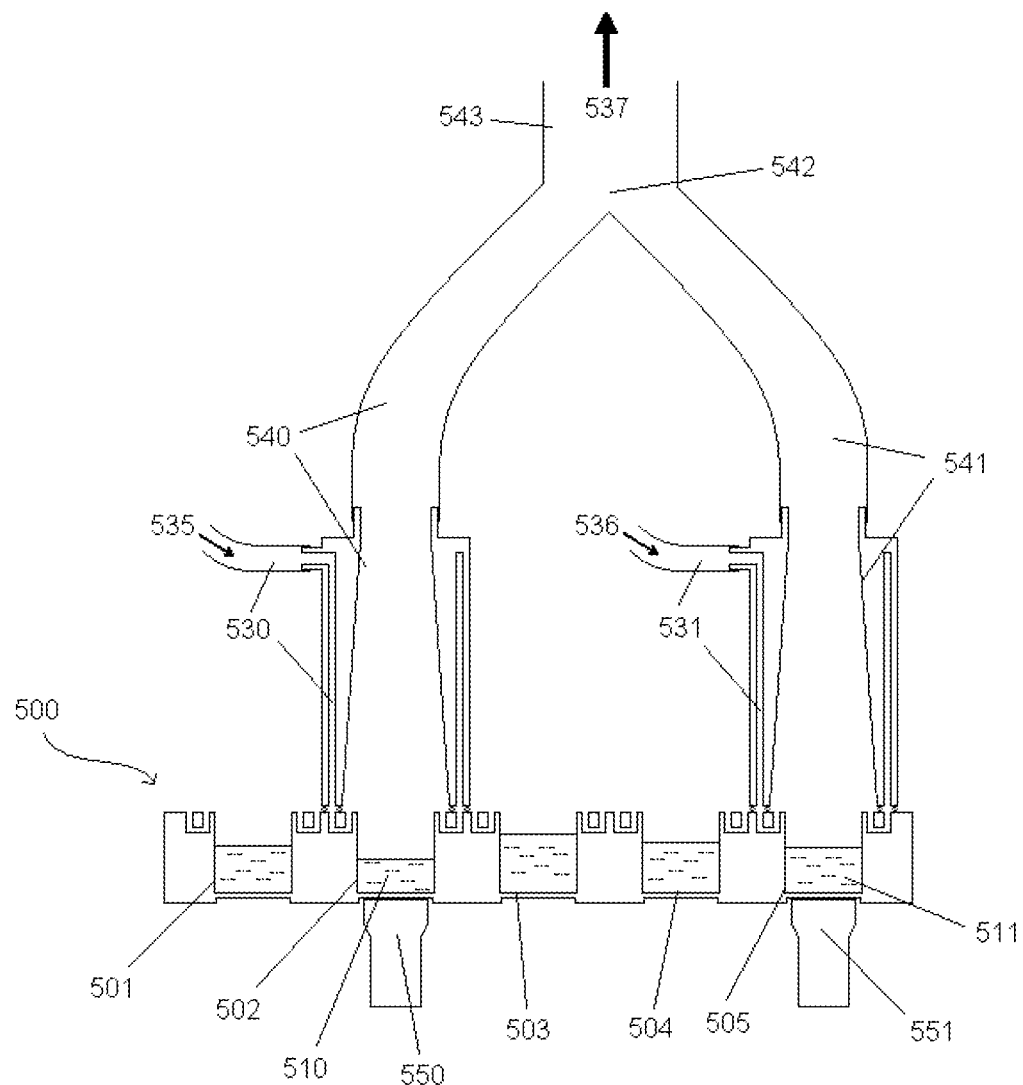

FIG. 5 is a schematic cross-sectional diagram of yet another embodiment of the invention. FIG. 5 depicts a well plate 500, comprising wells 501, 502, 503, 504, 505, each well being partially filled with a fluid. Well 502 is partially filled with liquid sample 510 and well 505 is partially filled with a solution containing a liquid standard, 511. A first acoustic transducer system 550 is arranged to deliver multiple pulses of acoustic energy focused on the surface region of liquid 510 so as to eject a stream of droplets of liquid sample from the surface, and a second acoustic transducer system 551 is arranged to deliver multiple pulses of acoustic energy focused on the surface region of liquid 511, so as to eject a stream of droplets of liquid standard from the surface. Coupled to well 502 is gas conduit 530 for providing a gas stream 535, and also coupled to well 502 is gas conduit 540 for guiding gas 535 away from the well 502. Coupled to well 505 is gas conduit 531 for providing a gas stream 536, and also coupled to well 505 is gas conduit 541 for guiding gas 536 away from the well 505. Channels are formed within well plate 500 connecting gas conduit 530 to gas conduit 540, and connecting gas conduit 531 to gas conduit 541, in a similar way to the arrangement described in relation to the embodiment of FIG. 4. Droplets emitted from liquid sample 510 are entrained in gas stream 535 within gas conduit 540. Droplets emitted from liquid standard 511 are entrained in gas stream 536 within gas conduit 541. Gas conduits 540 and 541 are connected together at 542 and gas streams 535 and 536 are combined to form gas stream 537 which flows through gas conduit 543 which is connected to an inlet of an analysis device (not shown). Hence the stream of droplets of sample is combined with the stream of droplets of standard before they enter the analysis device. Gas 535 and gas 536 are high purity argon, although it will be appreciated that in other embodiments another suitable gas or gases may be used. Gas conduits 540, 541, 543 are arranged so that there are no abrupt changes of direction for the gas flowing within the conduits, and this ensures that no droplets contact any solid surface after leaving the well plate and before entering the analysis device.

As used herein, including in the claims, unless the context indicates otherwise, singular forms of the terms herein are to be construed as including the plural form and vice versa. For instance, unless the context indicates otherwise, a singular reference herein including in the claims, such as "a" or "an" means "one or more".

Throughout the description and claims of this specification, the words "comprise", "including", "having" and "contain" and variations of the words, for example "comprising" and "comprises" etc, mean "including but not limited to", and are not intended to (and do not) exclude other components.

It will be appreciated that variations to the foregoing embodiments of the invention can be made while still falling within the scope of the invention. Each feature disclosed in this specification, unless stated otherwise, may be replaced by alternative features serving the same, equivalent or similar purpose. Thus, unless stated otherwise, each feature disclosed is one example only of a generic series of equivalent or similar features.

The use of any and all examples, or exemplary language ("for instance", "such as", "for example" and like language) provided herein, is intended merely to better illustrate the invention and does not indicate a limitation on the scope of the invention unless otherwise claimed. No language in the specification should be construed as indicating any non-claimed element as essential to the practice of the invention.

The invention claimed is:

1. A sample introduction apparatus for an analysis device comprising:
   a solid surface of a sample support suitable for locating a quantity of liquid sample;
   an acoustic transducer arranged so that, in use, acoustic energy is emitted towards the solid surface;
   a gas supply arranged to supply a stream of gas; and
   a gas conduit arranged between the gas supply and the sample support and between the sample support and an inlet of the analysis device,
   wherein the solid surface of the sample support comprises a sample support site suitable for locating a quantity of liquid sample and the gas conduit is arranged to supply the stream of gas in the form of a gas curtain at least partially surrounding a volume adjacent the sample support site.

2. The apparatus of claim 1 wherein the gas conduit comprises a first gas conduit arranged between the gas supply and the sample support and a second gas conduit arranged between the sample support and an inlet of the analysis device.

3. The apparatus of claim 2 wherein, the sample support, the second gas conduit, the inlet of the analysis device and at least part of the first gas conduit are contained within an enclosure filled with an inert gas.

4. The apparatus of any of claim 1 wherein the solid surface of the sample support comprises a sample support site suitable for locating a quantity of liquid sample, the sample support site comprising one or more of an indentation, a protuberance, or a site having undergone surface treatment, and the sample support site is partially or fully contained within the gas conduit.

5. The apparatus of claim 1 wherein the sample support comprises an array of containment vessels.

6. The apparatus of claim 5 wherein multiple containment vessels in the array of containment vessels contain quantities of liquid sample and sheets of polymer film seal the quantities of liquid sample within the containment vessels.

7. The apparatus of claim 1 wherein the sample support comprises one or more sample support sites composed of inert material.

8. The apparatus of claim 1 wherein the stream of gas is arranged to pass through a portion of the sample support in one or more channels, the channels extending through a portion of the sample support.

9. The apparatus of claim 8 wherein the sample support site is an inside surface of a containment vessel and the channels extend within one or more side walls of the containment vessel.

10. The apparatus of claim 1 wherein the gas conduit comprises a first gas conduit arranged to supply the stream of gas in the form of a gas curtain at least partially surrounding a volume adjacent the sample support site by passing it through one or more channels, the channels extending through a portion of the sample support.

11. The apparatus of claim 10 wherein the gas conduit comprises a second gas conduit arranged to receive the gas emerging from the one or more channels and transport it to an inlet of the analysis device.

12. The apparatus of claim 2 wherein the second gas conduit extends axially a distance between 10 and 100 mm from the region of the sample to the analysis device.

13. The apparatus of claim 2 wherein the second gas conduit has an internal cross sectional area which reduces as the second gas conduit extends away from the sample support.

14. The apparatus of claim 1 further comprising a droplet modifier located between the sample support and an inlet of the analysis device, the droplet modifier being configured to remove solvent from droplets of liquid which pass through it.

15. The apparatus of claim 1 further comprising a controller and a mechanism for moving the relative position of the sample support and the acoustic transducer.

16. The apparatus of claim 1 wherein the analysis device is one of: an Atomic Absorption Spectrometer, an Inductively Coupled Plasma Optical Emission Spectrometer, an Inductively Coupled Plasma Mass Spectrometer, a Microwave Plasma Optical Emission Spectrometer, a Microwave Plasma Mass Spectrometer, an Atomic Fluorescence Spectrometer, and a Laser Enhanced Ionization Spectrometer.

* * * * *

UNITED STATES PATENT AND TRADEMARK OFFICE
CERTIFICATE OF CORRECTION

PATENT NO. : 9,804,183 B2  
APPLICATION NO. : 14/163541  
DATED : October 31, 2017  
INVENTOR(S) : Ruan Hattingh et al.

Page 1 of 1

It is certified that error appears in the above-identified patent and that said Letters Patent is hereby corrected as shown below:

In the Claims

Claim 4, Column 20, Line 1:
Replace "the apparatus of any of claim 1"
With --the apparatus of claim 1--

Signed and Sealed this
Twenty-sixth Day of November, 2019

Andrei Iancu
*Director of the United States Patent and Trademark Office*